(12) United States Patent
Aiyer

(10) Patent No.: US 10,584,372 B1
(45) Date of Patent: Mar. 10, 2020

(54) SENSOR DEVICE AND METHOD FOR LABEL-FREE DETECTION OF DOUBLE STRAND NUCLEOTIDES

(71) Applicant: Arun Ananth Aiyer, Fremont, CA (US)

(72) Inventor: Arun Ananth Aiyer, Fremont, CA (US)

( * ) Notice: Subject to any disclaimer, the term of this patent is extended or adjusted under 35 U.S.C. 154(b) by 190 days.

(21) Appl. No.: 15/875,222

(22) Filed: Jan. 19, 2018

Related U.S. Application Data

(60) Provisional application No. 62/448,082, filed on Jan. 19, 2017.

(51) Int. Cl.
| *C12Q 1/6825* | (2018.01) |
| *G01N 21/27* | (2006.01) |
| *G01N 21/45* | (2006.01) |
| *G01N 21/23* | (2006.01) |

(52) U.S. Cl.
CPC ........... *C12Q 1/6825* (2013.01); *G01N 21/23* (2013.01); *G01N 21/27* (2013.01); *G01N 21/45* (2013.01)

(58) Field of Classification Search
USPC ..................................... 250/338.1; 435/287.2
See application file for complete search history.

(56) References Cited

U.S. PATENT DOCUMENTS

| 2001/0046673 A1* | 11/2001 | French | C12Q 1/6827 435/6.11 |
| 2007/0220978 A1* | 9/2007 | Su | G01N 29/0681 73/632 |
| 2011/0080580 A1* | 4/2011 | Fermann | G01N 21/31 356/301 |
| 2015/0236784 A1* | 8/2015 | Vahala | H04B 10/2507 398/115 |

* cited by examiner

*Primary Examiner* — Jason C Olson

(57) ABSTRACT

A sensor device which is adapted for detecting target molecules having a target nucleic acid sequence located in nano/micro channels, comprises a THz source for exciting the target molecules and a heterodyne interferometer, having a detection frequency MHz, for probing the excited molecules. The nano-channel array in the sample holder is functionalized with electric field to linearize the target alleles and genes. The linearized molecules are exposed to THz field whereby the different vibrational modes of base pairs are resonantly excited. The excitation of base-breathing mode and base-shifting mode leads to differential induced dipole moments along and perpendicular to the double helix axis. This induced asymmetry in polarizability leads to optical anisotropy. The dipole-dipole interaction between adjacent bases affects polarizability along the helix axis and hence the intrinsic molecular anisotropy is a function of number of base pairs in the strand. The resulting birefringence can be measured using the heterodyne interferometer as a function of changes in the number of base pairs in the strand. Furthermore, a sensing method for detecting birefringence in terms of phase shift of the MHz signal, as a function of target molecule size, is described.

19 Claims, 12 Drawing Sheets

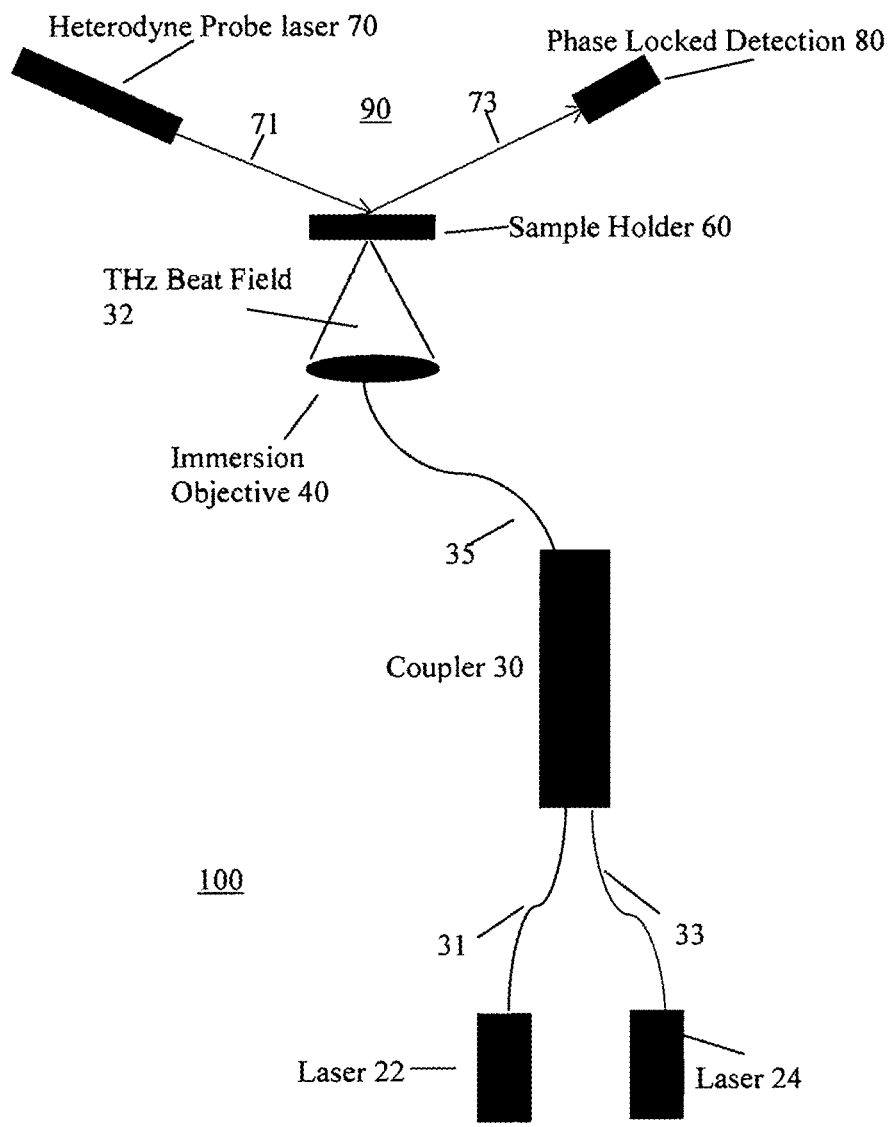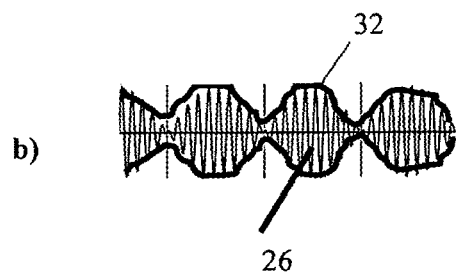
Figure 1

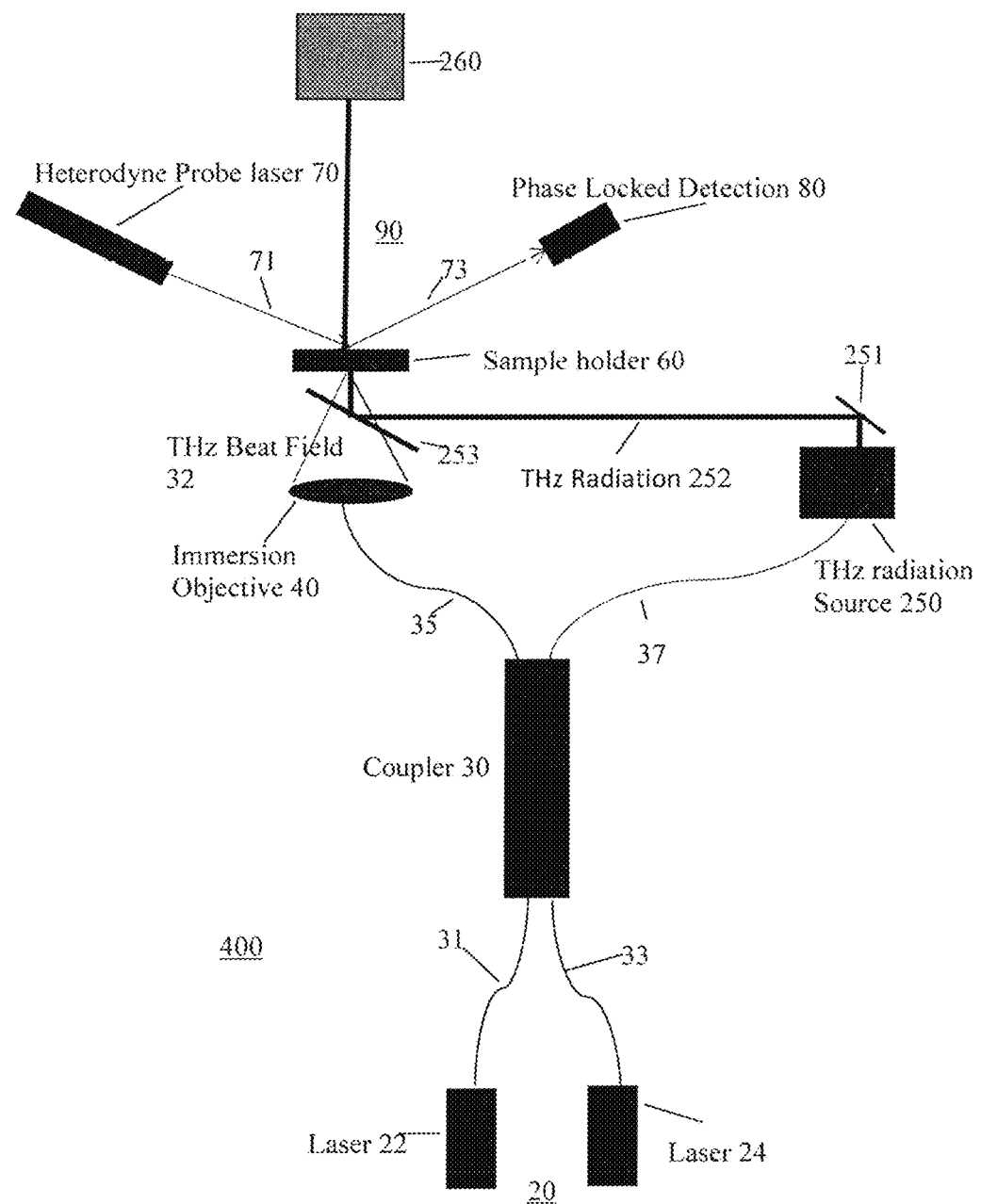
a)
Figure 6
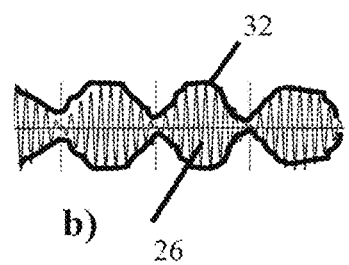
b)

Multiple Vibrational Modes in DNA at THz Frequencies (Source: Detecting Biomarkers by means of Terahertz Remote Sensing by Pauli E. Laine at University of Jyväskylä, Finland)

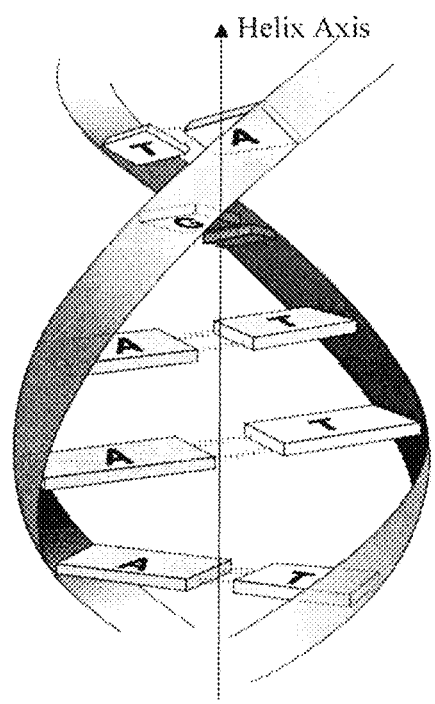
a)
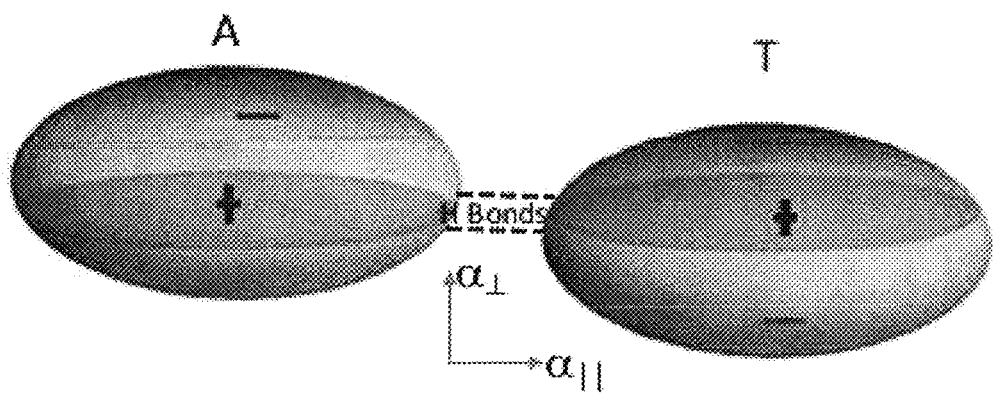
b)
Figure 8 This graphic shows a sketch of a DNA nucleic acid. The mostly planar molecules are divided into the positively charged molecule core (+) and the negatively charged outer π electron cloud (-). [22]

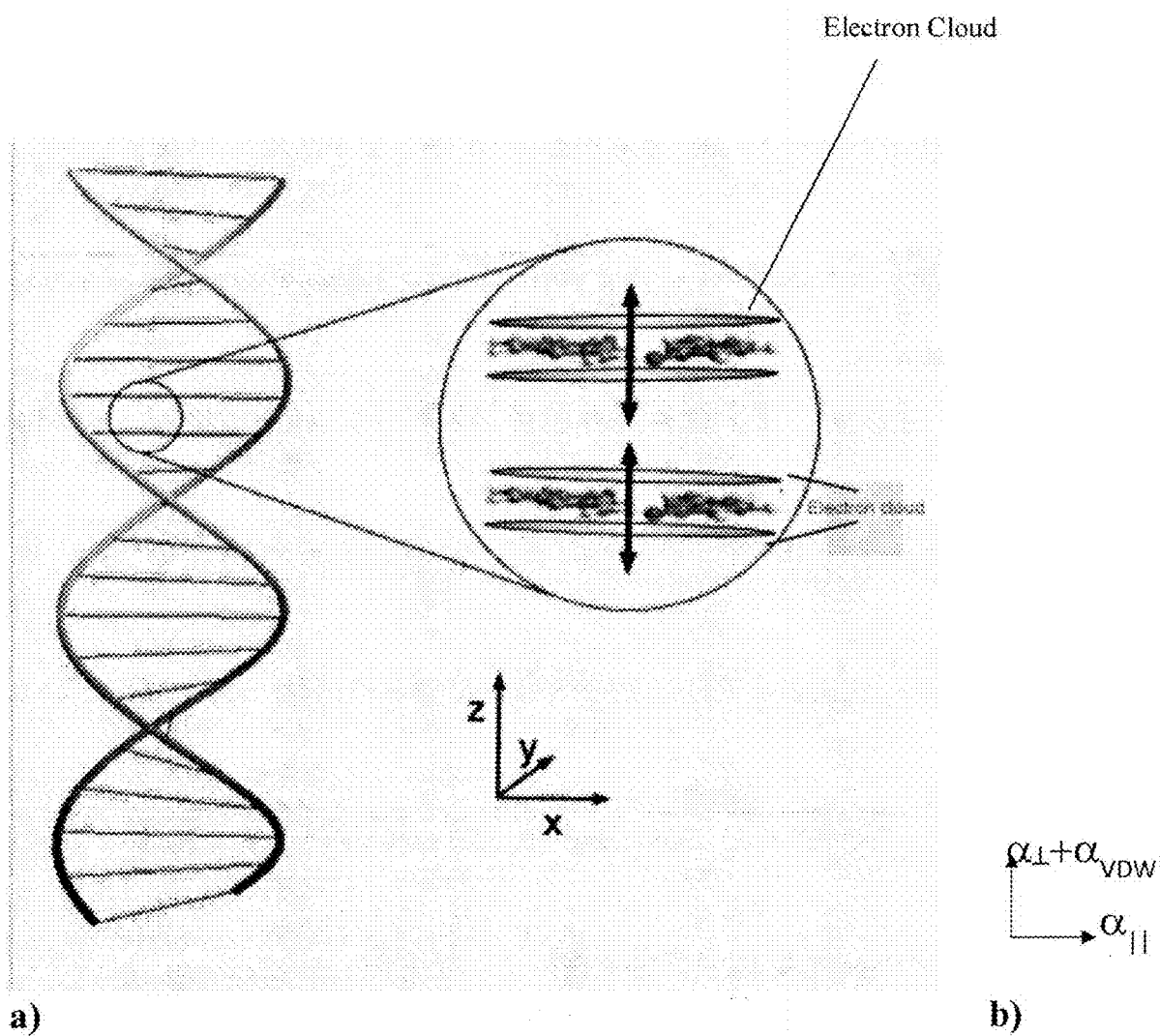
Figure 9 Sketch of a single DNA strand. Around the base pair core atoms is the (oval) outer electron cloud. The oscillation of these electron clouds is modelled here as non-permanent harmonic dipoles. [23]

(Schematic taken from open literature)

Figure 11 Beat signal from the probe beam

SENSOR DEVICE AND METHOD FOR LABEL-FREE DETECTION OF DOUBLE STRAND NUCLEOTIDES

CROSS-REFERENCE TO RELATED APPLICATIONS

This application claims the benefit of U.S. Provisional Patent Application No. 62/448,082 filed Jan. 19, 2017 by the present inventor, which is incorporated herein by reference in its entirety.

STATEMENT REGARDING FEDERALLY SPONSORED RESEARCH OR DEVELOPMENT

Not applicable

REFERENCE TO A SEQUENCE LISTING, A TABLE, OR A COMPUTER PROGRAM LISTING COMPACT DISC APPENDIX

Not applicable

FIELD OF THE INVENTION

The present invention relates to a sensor device for label-free detecting nucleic acid sequence length change, comprising terahertz (THz) field excitation and heterodyne technique. Furthermore, the present invention relates to a sensing method for label-free detecting nucleic acid sequences using the heterodyne interferometry. The invention further explicitly relates to method and apparatus for identifying gene mutations, ranging from single nucleotide polymerase (SNP) to large scale increase in base pair sequence repeats, through measurement of change in intrinsic birefringence of target genes. Applications of the invention could be in the fields of research and clinical nucleic acid sequencing or screening.

BACKGROUND OF THE INVENTION

With increased demand for rapid execution of gene sequencing in diagnostic and forensic areas, the need for label free detection and identification of alleles is growing. Label-free sensors circumvent the need for fluorescence modifications, and they are based on, e.g., detecting plasmon resonance, electrochemical conductance, mechanical resonance, micro cavity resonance or evanescent field-based absorption or direct absorption. However, these techniques may have disadvantages in terms of limited sensitivity or specificity or signal to noise (caused by sensor structure defects) because they all depend on properties of materials external to nuclei acids. Thus, there is need for a sensor that only utilizes property(ies) unique to the DNA molecule.

PRIOR ART

It is generally known that specific detection of nucleic acids, like DNA and RNA, is an important research and clinical goal as nucleic acids act to encode and regulate the expression of genes. Conventional detection techniques are based on detecting label or marker substances, or they use label-free sensors. Label-based sensors use, e.g., fluorescence-based assays to localize and quantitate nucleic acid molecules of interest. However, functionalizing oligonucleotides with fluorescent labels is typically a complex and expensive process that often skews physical and chemical properties, in turn affecting quantitative readout. Label-free sensors circumvent the need for fluorescence modifications, and they are based on, e.g., detecting plasmon resonance, electrochemical conductance or phonon resonance. However, these techniques may have disadvantages in terms lower sensitivity or specificity. A promising label-free sensor comprises of exploiting the various vibrational modes in nucleic acids. It is known that the base pairs in a double helix have vibrational modes such as base roll, proper twist, base breathing and base shift and that these modes respond to THz excitation. Significant amount of work has been done on label-free sensing of DNA using THz absorption spectra. However, as a general disadvantage, length-specific detection by direct absorption measurement alone, faces important challenges: limited sensitivity and specificity. This is mainly because, the THz radiations are absorbed by the host reagent in which these target molecules are usually present. Therefore, label-free sensing based on absorption signature must fight S/N issues. One may improve these by using pulsed THz source; which could be cost prohibitive for point of care service as well as lab based service. Another label-free sensor is based on measuring birefringence of target molecules after exposing them to THz fields. Prior art exploring this are given in these references. As noted above this method also suffers from S/N issues arising from background absorption. Use of other label-free sensing approaches such as extraordinary acoustic Raman (EAR), Whispering Gallery Mode have also been reported in literature.

SUMMARY OF THE INVENTION

An objective of the invention is to provide an improved sensor device for detecting mass variation in nucleic acid base pair sequence, avoiding limitations of conventional techniques. An additional objective of the invention is to provide a sensor device having an increased specificity, sensitivity & reusability and which enables rapid information turnaround. Furthermore, an objective is to provide an improved sensing method for detecting change in helix length or number of base pair length in alleles and genes, avoiding limitations of conventional techniques.

According to a first general aspect of the invention, the above objectives are solved by a sensor device, which is adapted for detecting target molecules having a target nucleic acid sequence length, comprising optical resonance excitation practice, optical phase measurement systems and practices and absorption measurement. The target molecules are exposed to THz electromagnetic fields and the induced birefringence of the excited target molecules are probed with MHz heterodyne interferometer (HI) for length specific molecular birefringence. The THz excitation of target molecules is brought about via evanescent fields and direct illumination. To achieve this, the excitation system would consist of two laser beams that can be mixed to produce tunable THz beat frequency. Part of the mixed signal is used with a photo mixer to generate THz radiation and the other part would be used for generating evanescent field beating at THz frequency. The evanescent field generator is a compact microscope with an objective having appropriate NA to generate evanescent field in the area where the target nuclei acid molecules/genes are located. Because of the frequency difference, the evanescent field generated by each laser will mix to generate THz beat field. The photo mixer is part of a commercially available THz source that is tunable from a few hundred GHz to 3 THz.

The flatness of the base pairs and the conjugation of their π electron system makes the DNA molecules highly polarizable. That enables induction of dipole moments along their planes (base breathing mode). The presence of these dipoles leads to Van der Waals interaction between adjacent base pairs (base shifting mode). Given the fact that the VDW is proportional to $1/r^6$, the dipole coupling between the adjacent flat bases are stronger leading to stronger stacking by several Kcal/mol. This means that the response of the atoms in the target molecule to an electromagnetic field, along the helix axis will be different from that perpendicular to the axis and that leads to strand length dependent optical anisotropy of the DNA strand. When these modes that show resonance in THz regime are excited by THz e.m. fields, the induced optical anisotropy will result in enhanced intrinsic birefringence of the molecule. Thus, according to the invention, the sensor is adapted for detecting enhanced birefringence in response to excitation frequency and a birefringence differential resulting from length modification of the target molecule strands.

According to a second general aspect of the invention, the above objectives are solved by a sensing method for detecting target molecules having nucleic acid sequences, wherein a sample liquid with target molecules to be investigated is applied to a nano channel array part of the sensor device and exposed to THz field according to the above first aspect of the invention, birefringence of the target molecule in the sample liquid in the array is measured with respect to the reference sample liquid using a heterodyne interferometer (HI) and change in the length of target molecules are detected by measuring the phase shift in the HI signal.

The invention provides for nucleic acid detection with a label-free sensor which circumvents costly fluorophore functionalization steps associated with conventional tests by utilizing sensitive detection limits provided by the HI sensor. The sensor resolution enables it to distinguish change in sequence length by single base pair and birefringence differential brought upon by single nucleotide polymorphisms (SNPs).

With the invention, the advantages of THz enhanced birefringence are combined with high sensitive HI detection to construct an integrated sensor for label-free allele/gene readouts.

Strategically, two types of THz fields can be used in the invention. According to a first preferred variant, a THz beat field could be generated by mixing two visible or NIR laser beams separated in frequency by THz. This variant has the advantage that mature optical technology is used in generating these THz fields and that their frequency can be swept from sub THz to THz by tuning the output frequency of one or both lasers. According to a second variant, the target molecules are exposed to THz radiation generated by the beat frequency in conjunction with a photo-mixer. According to a third variant, the target molecules are exposed to both THz beat field and THz radiation field simultaneously for simultaneous birefringence and absorption measurements.

With the beat frequency approach of the first variant, no genotoxicity of the target molecule associated with THz radiation absorption could occur. However, the presence of optical frequencies could lead to denaturing of target DNA strand. By using and sweeping through proper optical frequencies one could potentially control the denature/re-hybridization occurrences and the degree to which they occur in a strand. This feature could be used advantageously in the invention [42].

With the third variant, changes in target molecule sequence can be monitored with both phase shift and absorption change measurements. For lower concentration, phase shift measurement would be more effective while for higher concentration sample absorption measurement would be better suited.

Another embodiment of the invention would employ no THz field excitation. Changes in nucleic acid sequence length will be detected with heterodyne interferometry only using Effective Medium Theory (EMT) principles.

In summary, for real-time, label-free nucleic acid detection, the inventive sensor device provides three major advantages over conventional label-free approaches: sensitivity, speed, and device reusability.

The sensitivity and reusability of the inventive sensor device show that the invention is suitable not only for laboratory investigations but also for real world diagnostic applications. By allowing the same type of DNA-functionalized nano arrays to be generally used for the detection of nucleic acid biomarker, consumable manufacturing costs are sharply reduced. By allowing the same physical device to be used for multiple operations, the number of devices needed by the end users is reduced. Consequently, the application of inventive sensor device to point of care diagnostics is facilitated.

BRIEF DESCRIPTION OF THE DRAWINGS

Further details and advantages of the invention are described in the following with reference to the attached drawings, which show in:

FIG. 1 is a schematic illustration of a sensor device according to an embodiment of the invention;

FIG. 6 is a schematic illustration of a sensor device according to a fourth embodiment of the invention;

FIG. 8 is a schematic representation of DNA double helix with base pairs and induced charge separation;

FIG. 9 is a graphic sketch illustrating dipole-dipole interaction between adjacent complimentary base pairs;

DETAILED DESCRIPTION OF THE PREFERRED EMBODIMENTS

Figure 2:
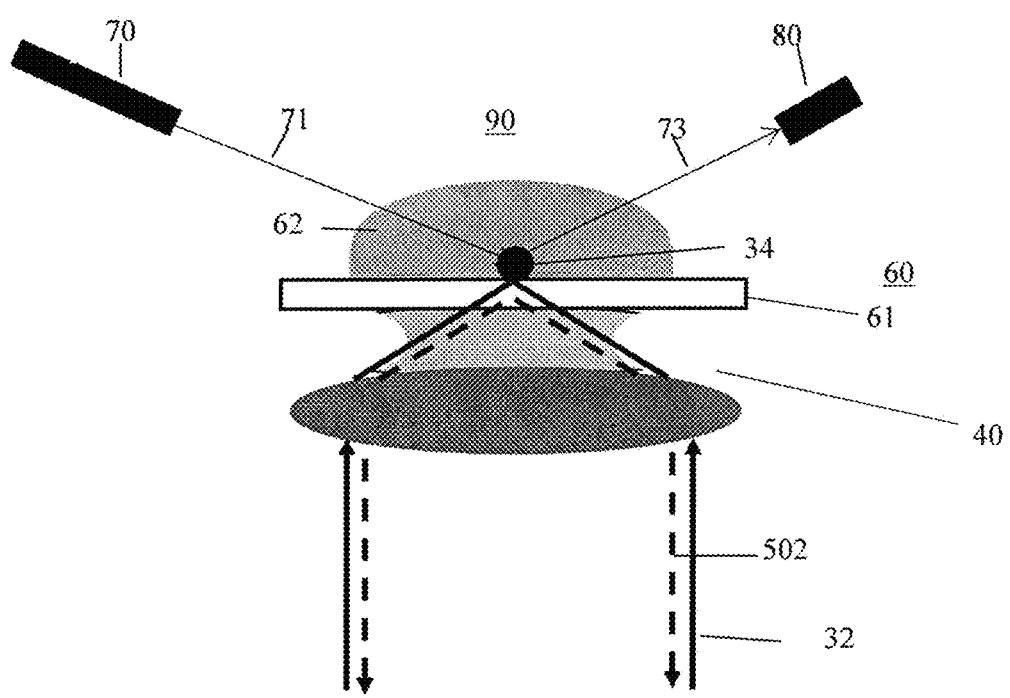
FIG. 2 is a schematic illustration of evanescent mode excitation of target molecules in the embodiment.

In the rendition given below, certain examples are given to illustrate many implementations and uses of the device and to explain specific details of the invention. Given the benefit of this disclosure, a person of ordinary skill in the art can put the invention into practice. Unless otherwise clear from the context, like numerals refer to similar structures in different figures. Moreover, those skilled in the art will acknowledge that embodiments described below may be executed in a multiplicity of ways. For example, the generation of THz beat frequency could be achieved with free space propagation of laser beams instead of fiber-optic guided wave propagation as shown in figures. Thus, through this disclosure we intend to include all possible execution of the invention.

All embodiments of the present invention incorporate apparatus and methods, for a robust sensor capable of sensitivity, speed, and device reusability. Details of operating the two laser sources used in the generation of THz fields, details of the probing laser used in the heterodyne interferometer, details of measuring phase shift of the heterodyne signal, and providing samples, in particular preparing nucleic acid strands, in arrayed nano channels are not described as they are known as such from prior art [31,32].

Origin of intrinsic birefringence in nucleic acids: A description of origin of birefringence in target nucleic acid and its dependence on base pair sequence length or molecular weight is given below before describing the invention.

FIGS. 8 and 9 schematically show the double helix of DNA molecule and charge cloud distribution of the base pair molecules. For the sake of discussion, only base pairs A and T are shown. Looking at FIG. 8a, one would notice that the bases are completely flat with their planes perpendicular to the helix axis and the edges of these flat bases are studded with hydrogen bond donor and acceptors. The flatness of the bases and the conjugation of the bases' n electron system makes the DNA molecules highly polarizable. In equilibrium, the charge centers of molecule core (+) and π electron cloud (−) coincide. An external field perturbation would cause the electron cloud to oscillate about the core, inducing a non-permanent dipole parallel to the helix axis. Referring to FIG. 8, presence of these dipoles (dipole-induced-dipole and induced-dipole-induced-dipole attractions) leads to Van der Waals (VDW) interaction between adjacent base pairs and given the fact that the VDW force is proportional to $1/r^6$, the dipole coupling between the adjacent flat bases are stronger leading to stronger stacking by several Kcal/mol.

An external perturbation applied along the H bond will contribute to stretching of dumb bell cloud structure inducing a dipole of a different magnitude orthogonal to the helix axis. Studies have determined that $\alpha_\perp < \alpha_\parallel$ [33, 34, 35].

This means that the response of the atoms in the DNA molecule to an electromagnetic field along the helix axis will be different from that along the perpendicular direction. In other words, the presence of two orthogonal polarizabilities $+\vec{\alpha_\perp} + \vec{\alpha_{VDW}}$) and $\alpha_\parallel$ lead to intrinsic optical anisotropy which in turn manifests as dsDNA birefringence. Here, $\alpha_\perp$ refers to the polarizability induced in π electron cloud and $\alpha_{VDW}$ is the polarizability resulting from coupling of adjacent oscillators [23].

Thus induction of dipole moments of differing values, along and perpendicular to base pair planes, occurs in the presence of external perturbations. These are represented by polarizability vectors $\alpha_\perp$, $\alpha_{VDW}$ and $\alpha_\parallel$ in FIGS. 8b and 9b. This differential response leads to optical anisotropy of the DNA strand and its intrinsic birefringence.

Figure 7:
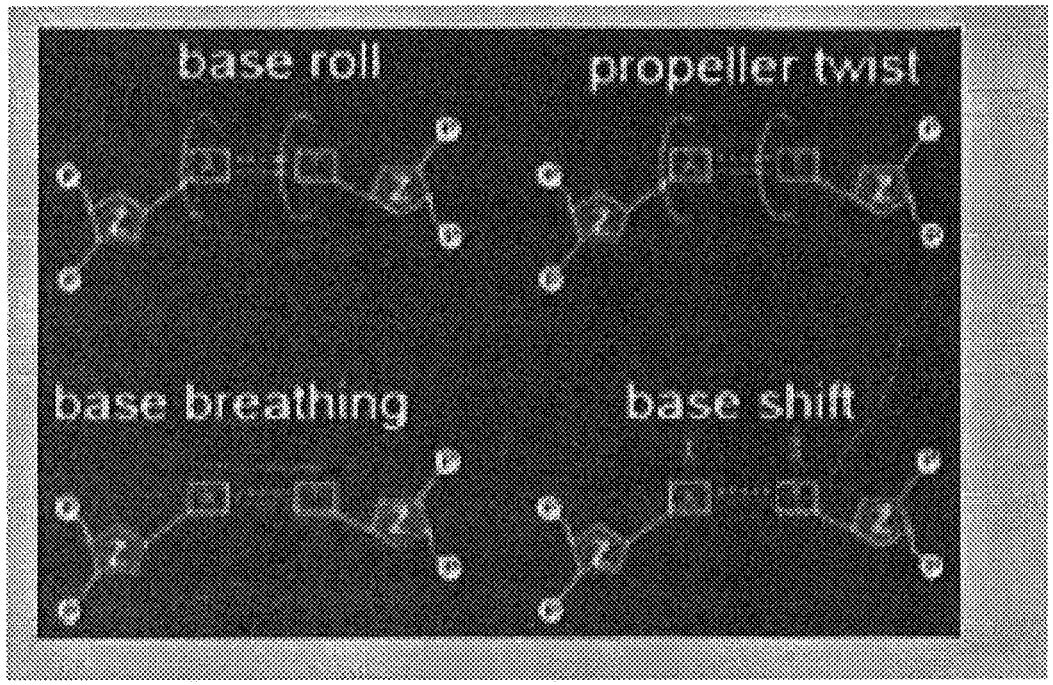
FIG. 7 is a visual representation of multiple vibrational modes in DNA.

FIG. 7 shows different vibrational modes that could be excited in dsDNA molecules. Base breathing and base shift are fundamental modes and the other two modes contribute components to these fundamental modes. These modes show resonances at THz frequencies [12,13,15,23]. Therefore, target nucleic acids exposed to THz field would display birefringence.

Additionally, the neighboring base pairs seen in DNA strands, schematically shown in FIGS. 7a and 8a, can be thought to form a series of harmonic oscillators. Perturbation modeling in [16] shows that DNA molecules undergoing THz oscillation along the base pair plane would couple some of the energy in the orthogonal direction. Thus, excitation of breathing mode would generate base shifting oscillations and vice versa. Once excited, these oscillators could be coupled to each other via dipole-dipole interaction. Coupling between multiple oscillators (base pairs) will influence the binding energy of the target DNA strand and hence its polarizability, differentially along and perpendicular to the helix axis. Thus, from classical point of view, the induced optical anisotropy or birefringence in a target allele or gene would be influenced by the number of base pairs present in the allele or gene. From quantum-mechanical point of view, the coupling can be viewed as entanglement between base pairs. Since the polarizabilities of bases A, T, C and G in x, y, z directions are different, different sequences will cause variations in the amount of entanglement in the chain of bases. The degree of entanglement determines the strength of molecular binding. This means that optical anisotropy will be different for target strands with different base pair sequences [23].

The intrinsic birefringence of the DNA molecular strand can be expressed as $$\Delta n_{DNA} = 4\pi(\alpha_\perp - \alpha_\parallel)/n_{DNA} \quad (1)$$

where the $\alpha$s are the polarizability density of the molecule perpendicular and parallel to the base plane. Density is defined as $N_0/V$ where $N_0$ is the number of base pairs in volume V [34].

From equation (1) and from equations (16) and (17) in [23] one can interpret that the degree of birefringence exhibited by a DNA strand is influenced by the number of base pairs in a strand [14]. Based on work reported in [24,16,36] the optical anisotropy of dsDNA would be influenced by THz field and the change in strand birefringence could be influenced by number of BPs present in the strand. Since CG bonds are stronger than AT bonds, sequences rich in CG or GC pairs are expected to display higher anisotropy than those rich in AT/TA pairs [14]. Thus, optical birefringence measurement in the presence of THz field could be developed as a new tool for the investigation of DNA strand length and would potentially provide a method for the label-free detection of the binding state of DNA and its use in fingerprinting. The inventive sensor is built to measure DNA birefringence in the presence of THz fields.

Sensor Device

Referring to FIG. 1, a schematic diagram of an exemplary DNA sensing device 100 is shown. It consists of light source 20, fiber-optic coupler 30, immersion microscope 40, sample holder 60 and heterodyne interferometric probing system 90.

The light source device 20 includes two laser sources 22 and 24, preferably continuous wave (cw) lasers, like e.g. a tunable distributed feedback laser (DFB) lasers operating at wavelength of 783+785 nm or 1533+1538 nm. Such a laser system is a commercially available from vendors like Toptica Photonics.

Sample excitation light from the laser sources 22/24 are coupled into the 1×2 optical coupler 30 via single mode fibers 31 and 33, where the two mix and optically beat. The mixed beams beating at the difference frequency exit the coupler via fiber 35. This fiber is connected to an immersion microscope objective 40 via appropriate connectors (not shown here). The objective 40 and the sample holder 60 are so arranged that the sample 62 with target molecules, located in 60 are exposed to the evanescent beat field. One or both laser sources 22/24 can be swept through a range of wavelengths such that the beat frequency can be scanned from 0 to 3 THz in steps of 1 MHz. The TI beat frequency 32 is schematically shown in FIG. 1b, FIG. 5b. 26 in these figures refer to the optical frequencies of the lasers 22 and 24. Such a system can be bought from Toptica Photonics.

The sample holder 60 in FIG. 2, comprises a dielectric substrate 61 like a quartz slide with necessary structures etched in it to allow for the allele or gene strands to be linearized and moved into region 34 where evanescent filed is present. The optical frequency differences in Lasers 22 and 24 make the evanescent field to beat at the respective difference frequency. The beat frequency can be tuned from 0 to THz. Detailed description of sample holder and strand linearization can be found in the referenced literature [31, 32,37,38].

For implementing the inventive sensing method for detecting changes in target allele or gene strand length, the substrate is prepared with sample-free host reagent environment in the nano-channels. The birefringence of the liquid is measured as function of THz beat frequencies. Next allele or gene populated reagent is placed in the nano-channels and exposed to the evanescent field created in the nano-channel space 34. The sample birefringence is measured again. Change in birefringence would indicate presence of target molecules in the sample liquid. For the same liquid concentration and for the same allele number density in region 34, change in birefringence would be detected, if the target molecule length changes.

Again referring to FIG. 2, target molecule birefringence is measured using measurement system 90. The system is a heterodyne interferometer. It consists of a probe laser 70 and a phase meter 80. The laser beam 71 exiting the laser 70 has two orthogonal polarizations. These are represented by 701 and 703 in FIG. 10. Optical frequency of one of the polarizations is different from that of the other polarization by ~KHz to MHz. The linearized molecules, in sample volume 62, when exposed to beam 71 will experience both electric fields. Because of the birefringence of the molecule, wavefront corresponding to each polarization will experience different phase velocities in the sample. The phase meter includes an analyzer polarizer for mixing the two polarizations, which when sensed by a photo-detector generates a typical beat signal at the difference frequency.

Figure 10:
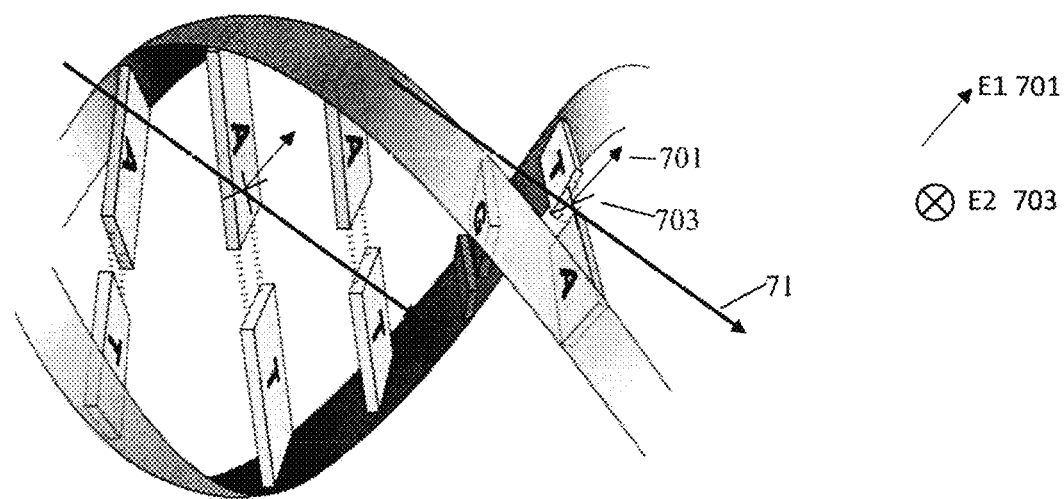
FIG. 10 illustrates orientation of polarization vectors of the laser beam used in Heterodyne interferometer with respect to base pair plane.
Figure 11:
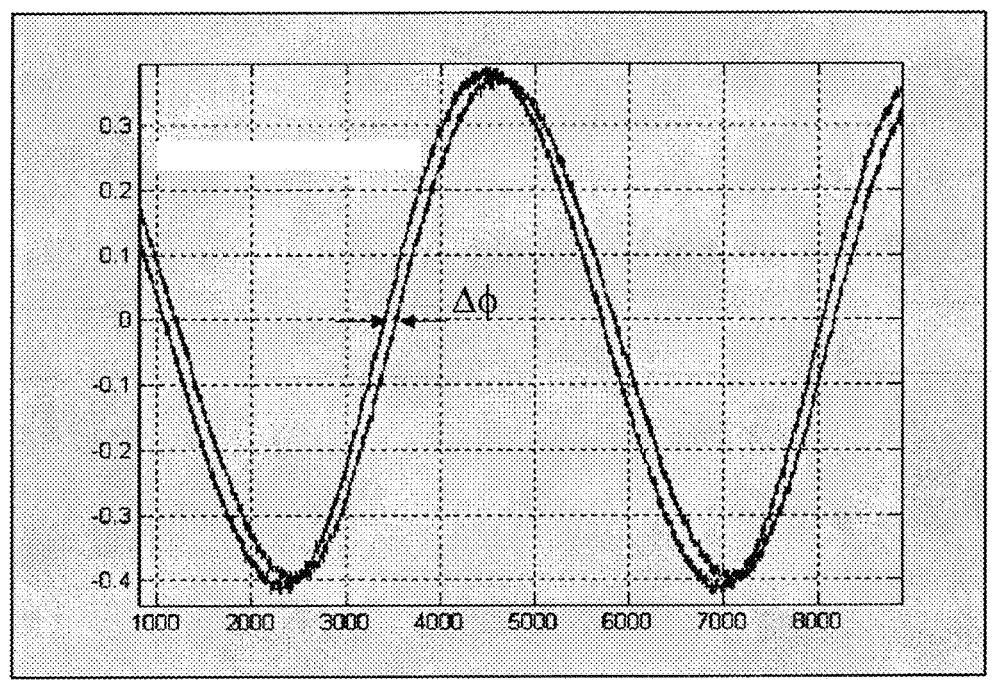
FIG. 11 is a graphic illustration of phase shift sensed by the MHz heterodyne interferometer.

Referring to FIG. 10, as an example, a DNA strand with 5 base pairs is shown along with the incident probe beam. The beam is composed of two polarizations, 701 and 703. 701 lies along the incidence plane and 703 is orthogonal to it i.e., ∥ and ⊥ to the plane of the paper respectively. For the orientation of the DNA strand shown in FIG. 10, the plane of each base pair is also orthogonal to paper plane. Because of difference in polarizabilities, induced by the THz evanescent field, along the H bond direction and along the helix axis in the π electron cloud, and the coupling between induced dipoles, the target molecule would exhibit optical anisotropy. Consequently, wavefront corresponding to each polarization in the probe beam will undergo different phase retardations as the beam interacts with the sample. By measuring phase difference between the two polarizations, the sample birefringence can be determined. To make that determination, in HI, the two polarizations are optically mixed and the resulting beat signal is detected and its phase measured using Phase Locked amplifier 80 (like those from Zurich Instruments). As the target molecule length changes or its characteristics changes, the beat signal will undergo a phase shift, as schematically shown in FIG. 11. The displacement between the two sinusoids represents the phase difference given by $$\Delta\phi = (2\pi/\lambda)\Delta n \cdot l \quad (2)$$

where 'l' is the sample thickness and $\Delta n$ is the molecule birefringence which is $$\Delta n_{allele} = \Delta\phi \cdot \lambda/(2\pi \cdot l) \quad (3)$$

The incidence angle of probe beam 70 could be set at a value between 0° to 90°. At normal incidence, anyone polarization will be either parallel or perpendicular to base plane. At angles other than normal incidence angle, polarization 701 sees both H bond stretching and π cloud distortion, while the polarization 703 sees only it cloud distortion. This is independent of the orientation of the strands with respect to the channel direction.

When all strands lie along the channels, then normal incidence would be the preferred angle for the probe beam 70.

Figure 3:
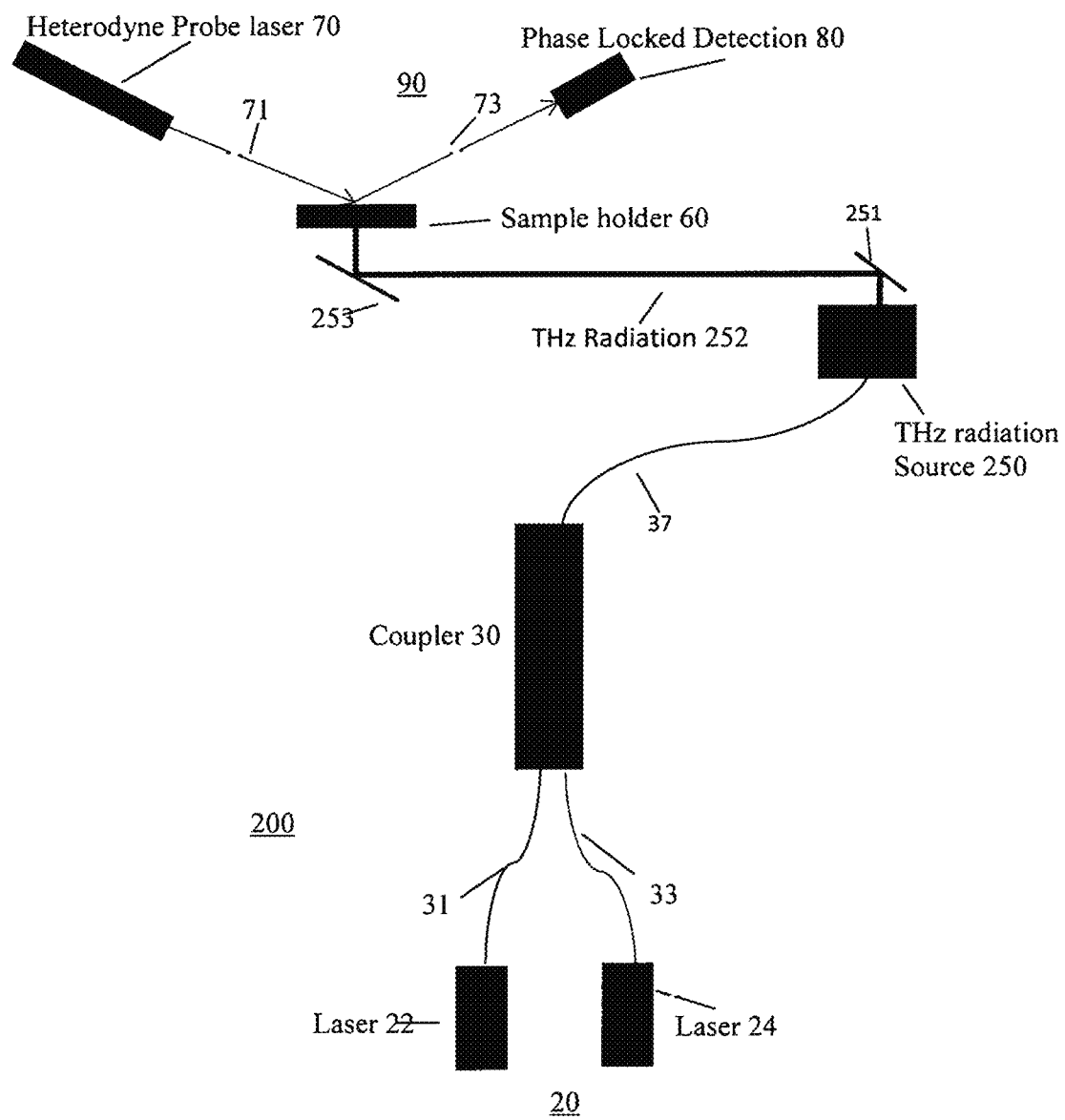
FIG. 3 is a schematic illustration of a sensor device per a second embodiment of the invention.

Sensing device 200 shown in FIG. 3 is a schematic illustration of second embodiment. It consists of light source 20, fiber-optic coupler 30, THz radiation source 250, sample holder 60 and heterodyne interferometric probing system 90.

The light source device 20 in sensor 200 includes two laser sources 22 and 24, preferably continuous wave (cw) lasers, like e.g. a tunable distributed feedback laser (DFB) lasers operating at wavelength of 783+785 nm or 1533+1538 nm.

Sample excitation light from the laser sources 22/24 are coupled into the 1×2 optical coupler 30 via single mode fibers 31 and 33, where the two mix and beat. The mixed beams beating at the difference frequency exit the coupler via fiber 37. This fiber is connected to a photo mixer/radiator via connectors (not shown here). Continuous-wave (cw) terahertz radiation is obtained by optical heterodyning in high-bandwidth photoconductors. The core component is the "photo-mixer," a microscopic metal-semiconductor-metal structure. Near-infrared laser light irradiates this structure at two adjacent frequencies. Applying a bias voltage to the metal electrodes then generates a photocurrent that oscillates at the beat frequency. An antenna structure surrounding the photo-mixer translates the oscillating photocurrent into the terahertz wave. State-of-the-art photo-mixers are based on either GaAs or InGaAs/InP and require laser wavelengths below the semiconductor bandgap (i.e. around 0.8 μm or 1.5 μm, respectively [39]. The THz beam 252 from source 250 is steered toward the sample holder 60 via steering and focusing optics 251 and 253, thus exposing sample 62 located in 60 to THz photon field. One or both laser sources 22/24 can be swept through a range of wavelengths such that the THz radiation can be scanned from 0 to 3 THz in steps of 1 MHz.

Figure 5:
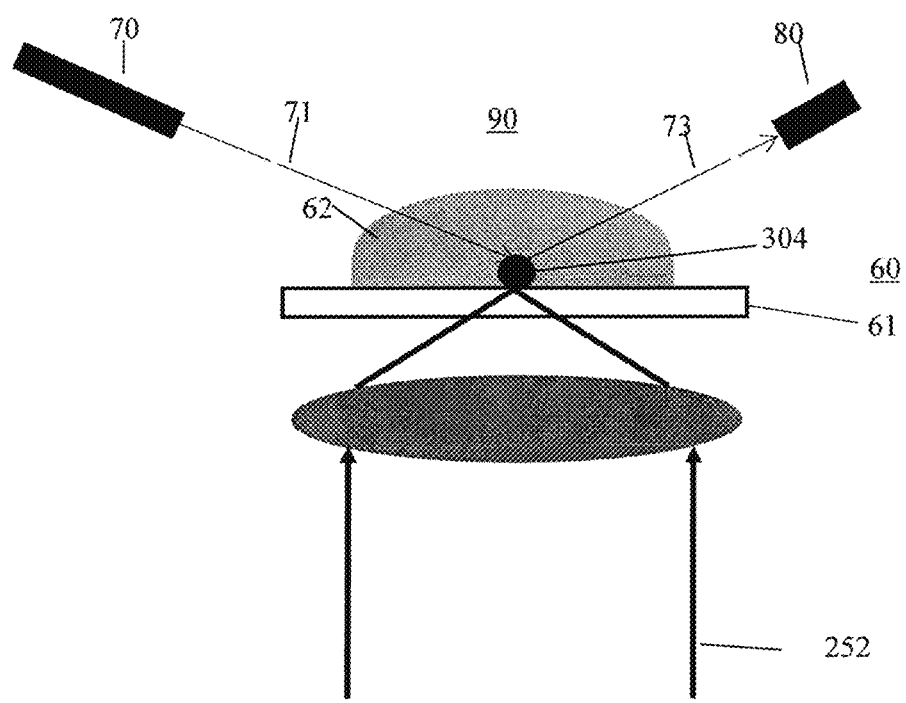
FIG. 5 is a schematic illustration of the THz irradiation focus system.

The second embodiment of inventive sensor is implemented as shown schematically in FIG. 3 and FIG. 5. The nano-channels in the substrate are prepared with target molecule free reagent environment. The birefringence of the liquid is measured as described above (section 0045), as a function of swept THz frequencies. Next, the reagent populated with allele or gene is placed in the nano-channels and exposed to the THz photon field created in focal volume 304. This field induces birefringence in the target molecules and the corresponding sample birefringence is measured again. Change in birefringence would indicate presence of target molecules in the nano-channel arrays. For the same liquid concentration and for the same allele number density in region 304, change in measured birefringence would be detected if the target nucleic acids length or its characteristic changes.

The second embodiment could be implemented by replacing the continuous wave (CW) THz source comprising of laser source 20, coupler 30, and photo-mixer/radiator 250 with a pulsed THz system similar to that provided by Toptica Photonics [39] or other vendors.

Figure 4:
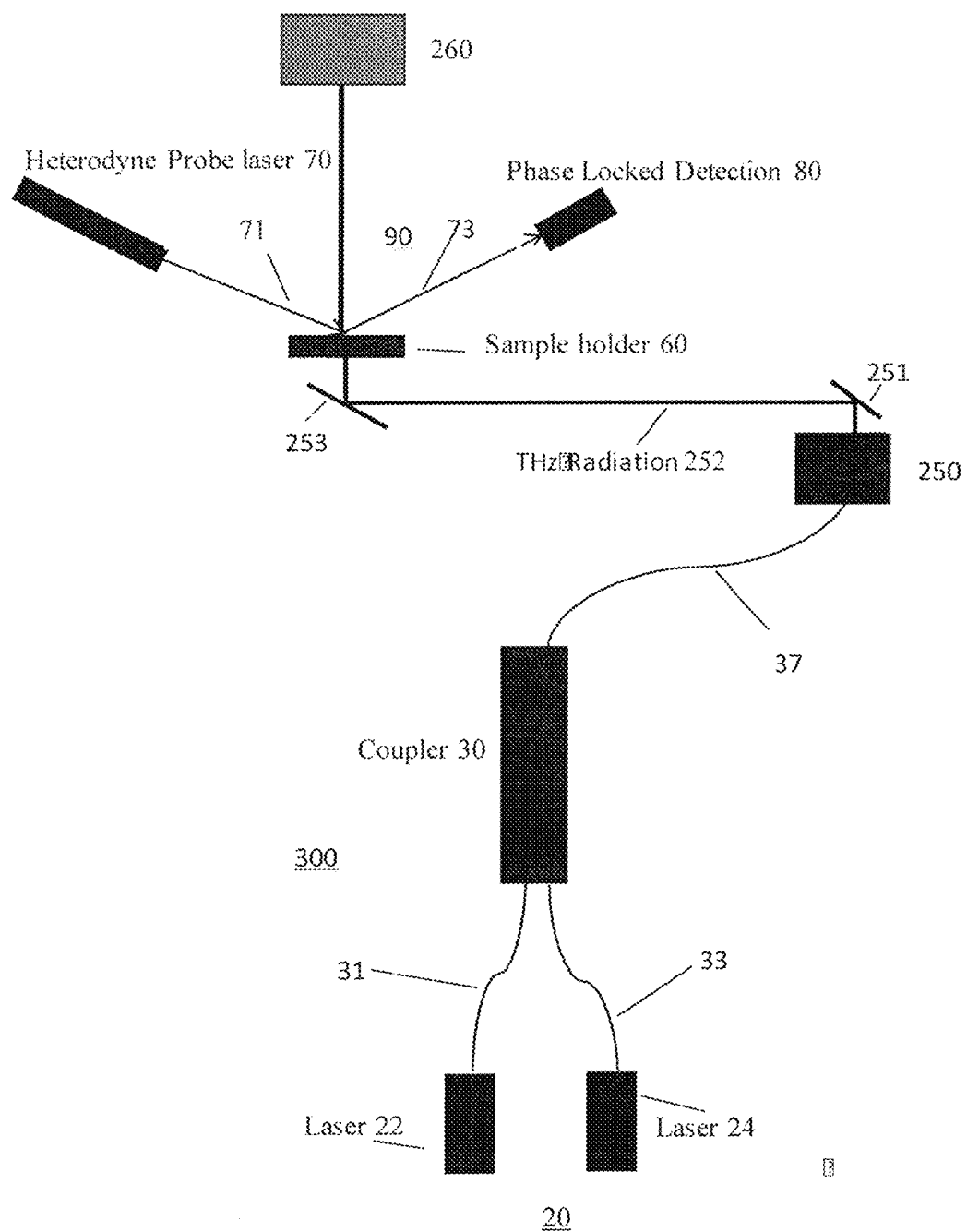
FIG. 4 is a schematic illustration of a sensor device according to a third embodiment of the invention.

In the third embodiment of the invented sensor 300, schematically represented by FIG. 4, THz transmission spectrum of the allele/gene sample is measured using a THz spectrometer 260 while system 90 measures the birefringence induced by the radiation 252. With this embodiment, a direct correlation between changes in absorption spectra and allele birefringence could be made.

In the fourth embodiment of the inventive system 400, shown in FIG. 6, the samples in the nano-channel sample holder 60, are exposed to both THz beat field and THz radiation field simultaneously. The excited sample is probed with system 90 for birefringence and with spectrometer 260 for absorption signatures. By adjusting the phase between the THz beat field and the THz radiation field, it would be possible to adjust the magnitude of induced polarization in target nucleic acids and hence their birefringence. Measurement of a direct correlation between changes in absorption spectra and allele birefringence is possible with this embodiment.

Figure 12:
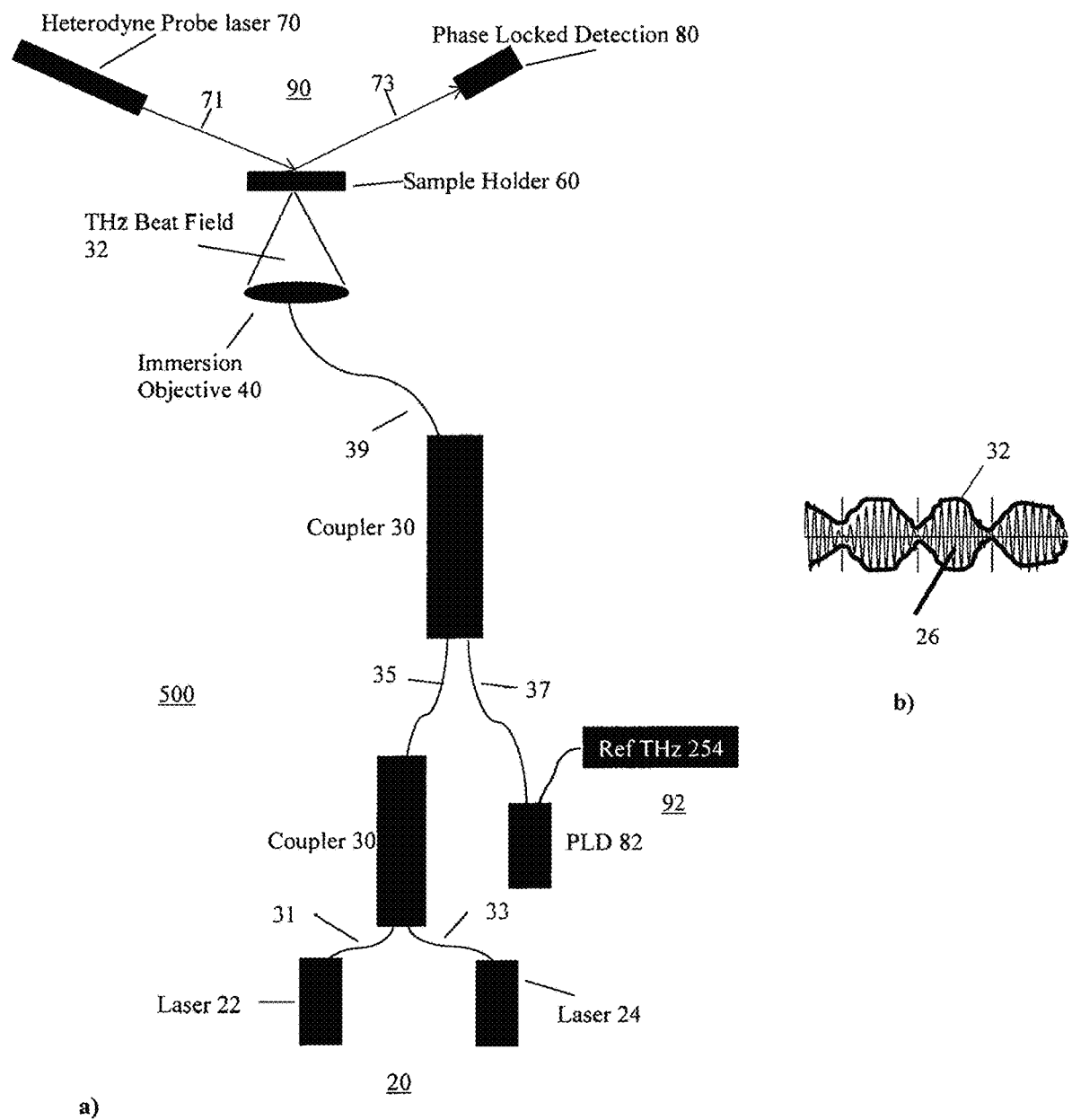
FIG. 12 is a schematic illustration of a sensor device according to a fifth embodiment of the invention.

The fifth embodiment of the inventive sensor 500, is shown schematically in FIG. 12. It consists of light source 20, two fiber-optic couplers 30, immersion microscope 40, sample holder 60, a phase lock amplifier 82 and heterodyne interferometric probing system 90.

The light source device 20 includes two laser sources 22 and 24, preferably continuous wave (cw) lasers, like e.g. a tunable distributed feedback laser (DFB) lasers operating at wavelength of 783+785 nm or 1533+1538 nm.

Sample excitation light from the laser sources 22/24 are coupled into the 1×2 optical coupler 30 via single mode fibers 31 and 33, where the two mix and beat. The mixed beams beating at the difference frequency exit the coupler via fiber 35 which is connected to another 1×2 coupler 30. The output of this coupler is connected to an immersion microscope objective 40 using appropriate connectors (not shown here). The objective 40 and the sample holder 60 are so arranged that the sample 62 located in 60 are exposed to the evanescent beat field. One or both laser sources 22/24 can be swept through a range of wavelengths such that the beat frequency can be scanned from 0 to 3 THz in steps of 1 MHz. The THz beat frequency 32 is schematically shown in FIG. 12b. 26 in this figures refer to the optical frequencies of the lasers 22 and 24.

In implementing the sensor system 500, the return beam 502 as shown in FIG. 2 is sent to a phase detection system 92 via fiber 39, coupler 30 and fiber 37. The detection system consists of a THz local oscillator 254, photo-mixer to sense the beat frequency in beam 502, phase lock amplifier or coherent detector 82.

With sensor 500, target molecule birefringence would be detected with phase detection system 92. The pump beam 32 itself would be used as probe beam for 92. This is possible since the resonance or near resonance excitation induced by beam 32 will induce a phase shift in return beam 502 which would be measured using phase locked detector 82 [40]. Thus, this embodiment would make sensor 500 a complete common path system.

Furthermore, HI system 90 working in conjunction with system 92 would provide the sensor 500 with auto-check/auto-calibration features that are not reported elsewhere.

The sixth embodiment of the inventive sensor, not shown schematically here, is a system that embraces all features shown in system 400 in fourth embodiment and system 500 in fifth embodiment.

With the sixth embodiment, both birefringence and absorption measurements could be achieved simultaneously or in tandem.

The seventh embodiment of the invention could be implemented using HI probe system 90 shown in any one of the previous embodiments and therefore, do not have a separate figure assigned to it. The measurement principle is based on Effective Medium Approximation [41]. Per this theory, the presence of target molecule of a certain length is detected by change in the refractive index of the host reagent brought about by fractional change in the effective dielectric constant of the host. To ensure that the measurement relates only to the change in the effective refractive index of the host reagent, an analyzer polarizer is positioned in the path of beam 71. The created beat signal upon interrogating the sample mixture will undergo a phase shift. Measuring this phase difference, comprising measuring a phase of the detected beat frequency relative to a phase of a beat frequency of a reference signal.

The previous examples and embodiments are representative examples of the spirit of the present invention and should not be construed as limiting the scope of the invention. Furthermore, any improvements, enhancements, different physical implementation, different operation sequence, combinations thereof and equivalent counterparts that could be thought of after examining the drawings and understanding the specifications are within the true spirit and scope of the present invention.

Terms used in this disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description of embodiments, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in this disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that, various changes, substitutions, and alterations could be made hereto without departing from the spirit and scope of the present disclosure.

What is claimed:

1. A sensor device which is adapted for detecting target molecules having a target nucleic acid sequence length based on measuring a phase shift in beat signals generated by mixing light beams of differing frequencies, comprising:
   a. two source lasers in near IR (NIR) region with frequency difference varying from 0 Hz to THz;
   b. one or more fiber-optic couplers for mixing and propagating the two laser frequencies;
   c. a fiber coupled immersion microscope objective for generating evanescent THz beat field;
   d. a THz photo-mixer and radiator;
   e. THz reflectors;
   f. a substrate comprising nano-fluidic and macro-fluidic channel arrays, having thereon a layer of host reagent with target DNA strands to be linearized and measured;
   g. an evanescent microscope configured to expose target nucleic acids to THz beat frequency and/or to THz radiation frequency;
   h. a polarized light emission optical system, comprising a heterodyne laser, configured to emitting a light signal in predetermined polarization states or in single state toward a target to be measured;
   i. a polarized light detection optical system, comprising an analyzer polarizer, and configured to detect the light signal from the polarized light emission optical system after interacting with the target, the light signal including birefringence information on the target nucleic acids, wherein the birefringence information is polarimetrically analyzed by detecting a beat frequency of two orthogonally polarized modes of laser light from the analyzer polarizer;
   j. a photo detector configured to convert the light signal from the polarized light detection optical system into an electric signal and further configured to detect the electric signal;
   k. a phasemeter configured to measure a relative phase difference, comprising measuring a phase of the detected beat frequency relative to a phase of a beat frequency of a reference signal, the beat frequency of the reference signal comprising a difference in frequency between the two orthogonally polarized modes of laser light;
   l. the phasemeter further configured to detect, a target allele/gene by correlating the relative phase difference with a change in effective refractive index caused by change in number of base pairs or strand sequence change in target species in a host reagent;
   m. the phasemeter further configured to detect a target allele/gene by correlating the relative phase difference with a change in effective dielectric constant caused by fractional change in a composition of the host reagent;
   n. a sensor device configured to perform polarimetric analyses of a returning THz beat signal, wherein the polarimetric analysis is configured to extract birefringence information on target nucleic acids; and
   o. a THz spectrometer configured to measure transmission spectra of THz radiation that passes through the target molecules.

2. The sensor as recited in claim 1 wherein said nano-fluidic and micro-fluidic channel arrays are a plurality of etched channels in dielectric substrate material or semiconductor substrate material.

3. The sensor as recited in claim 1 wherein the NIR lasers are optically mixed in a fiber-optic coupler to generate THz beat frequency.

4. The sensor as recited in claim 1 or claim 3 wherein the sensor device is configured to focus the beat signal on to the target molecule using immersion objective.

5. The sensor as recited in claim 4 wherein a beat field excites the targets in channel arrays via evanescent beat field.

6. The sensor as recited in claim 5 wherein the beat field induced birefringence of target molecules is measured using the phase shift of the beat frequency from the heterodyne laser relative to a phase of a beat frequency of a reference signal, the beat frequency of the reference signal comprising a difference in frequency between the two orthogonally polarized modes of laser light.

7. The sensor as recited in claim 1 wherein the NIR lasers are optically mixed in a photo-mixer/radiator to generate and propagate THz radiation.

8. The sensor as recited in claim 1 or claim 7 wherein the THz radiation signal is focused on to the target molecule using THz optics.

9. The sensor as recited in claim 5 wherein the THz field induced birefringence of target molecules is measured using the phase shift of the beat frequency from the heterodyne probe laser relative to a phase of a beat frequency of a reference signal, the beat frequency of the reference signal comprising a difference in frequency between the two orthogonally polarized modes of laser light.

10. The sensor as recited in claim 1 wherein the photo detector measures absorption spectra of THz radiation passing through the sample.

11. The sensor as recited in claim 1 wherein the sensor device measures phase of a reflected THz beat signal, that carries birefringence information on the target nucleic acids.

12. The sensor as recited in claim 1 wherein the birefringence of the target molecules is measured as a function of frequency of an excitation source.

13. A method for inducing birefringence in genes and alleles of different lengths in micro/nano fluidic (MNF) channel array comprising:
   a. mixing two frequency shifted near IR (NIR) laser beams through a fiber-optic coupler to generate beat frequencies in sub-THz to THz range;
   b. propagating a portion of mixed beam through an immersion objective to a micro/nano fluidic channel having thereon a layer of host reagent populated with DNA species;

c. reflecting the mixed beam from the MNF channels at angles greater than a critical angle generating evanescent field at beat frequency in MNF channels;
d. propagating a portion of the mixed beam to a photomixer/antenna to generate THz radiation
e. propagating the THz radiation through MNF channel having thereon a layer of host reagent populated with DNA species; and
f. inducing birefringence in the tartlet molecules through resonance excitation of vibrational mode in DNA base pairs with one or both THz fields.

14. The method of claim 13 further comprising sensing induced birefringence in genes and alleles, includes measuring phase shift in probing beams comprising:
   a. propagating two orthogonally polarized modes of laser light differing in wavelength through a nano/micro fluidic channel having thereon a layer of host reagent populated with DNA species;
   b. transmitting a portion of each of the two modes of laser light through an analyzer polarizer after their emergence from the fluidic channel;
   c. detecting a beat frequency of the two orthogonally polarized modes of laser light from the polarizing analyzer;
   d. measuring a relative phase difference, comprising measuring a phase of the detected beat frequency relative to a phase of a beat frequency of a reference signal, the beat frequency of the reference signal comprising a difference in frequency between the two orthogonally polarized modes of laser light; and
   e. detecting a DNA strand by correlating the relative phase difference with a change in effective refractive index caused by inclusion of the selected gene/allele in the host reagent.

15. The method of claim 13 further comprising sensing induced birefringence in genes and alleles of different length based on measuring phase shift in the beat frequency of excitation beams, comprising:
   a. mixing two frequency shifted NIR laser beams through a fiber-optic coupler to generate beat frequencies in sub-THz to THz range;
   b. propagating a portion of mixed beam through an immersion objective to a micro/nano fluidic channel having thereon a layer of host reagent populated with DNA species;
   c. reflecting the mixed beam from the MNF channels at angles greater than the critical angle generating evanescent field at beat frequency in MNF channels, wherein the evanescent fields of the mixed beam experiencing the birefringence of the species populating the host reagent;
   d. propagating the reflected beam back through the immersion microscope and optical coupler into a phase detector, wherein the phase detector detects a phase shift between the incident THz beat frequency and reflected THz beat frequency; and
   e. detecting a DNA strand by correlating the relative phase difference with a change in effective refractive index caused by inclusion of the selected gene/allele in the host reagent.

16. A method for detecting genes and alleles of different lengths in micro/nano fluidic (MNF) channel array that uses absorption and phase measurements comprising:
   a. mixing two frequency shifted near IR (NIR) laser beams through a fiber-optic coupler to generate beat frequencies in sub-THz to THz range;
   b. propagating a portion of the mixed beam to a photomixer/antenna to generate THz radiation;
   c. propagating the THz radiation through MNF channel having thereon a layer of host reagent populated with DNA species; and
   d. measuring the absorption spectra of samples using a THz spectrometer; and
   e. correlating the absorption spectra to phase difference measurements.

17. The method of claim 16 further comprising sensing genes and alleles of different lengths in micro/nano fluidic (MNF) channel array comprising:
   a. excitation of the target species using THz beat field;
   b. excitation of the target species using THz radiation field;
   c. measurement of induced birefringence in the target species by measuring phase shift between orthogonal polarizations in a probe beam that interrogates target species;
   d. measurement of induced birefringence in the target species by measuring phase shift of the reflected THz beat signal;
   e. measurement of absorption signatures of the target species;
   f. correlation between phase shift measurements and spectral absorption measurement; and
   g. simultaneous detection and measurement of phase shift and absorption spectra of the target species.

18. The method of claim 17 further comprising sensing induced birefringence in genes and alleles of different lengths in micro/nano fluidic (MNF) channel array comprising:
   a. excitation of the target species using THz beat field;
   b. excitation of the target species using THz radiation field;
   c. adjusting the phase between the THz beat field and the THz radiation field;
   d. measurement of resultant induced birefringence in the target species by measuring phase shift between orthogonal polarizations in a probe beam that interrogates target species;
   e. measurement of absorption signatures of the target species; and
   f. correlation between phase shift measurements and spectral absorption measurement.

19. A method of claim 13 further comprising sensing change in refractive-index in host reagent based-on measuring phase shift in probing beams comprising:
   a. mixing two orthogonally polarized modes of laser light differing in wavelength through an analyzer polarizer and propagating the mixed modes through a nano/micro fluidic channel having thereon a layer of host reagent populated with DNA species;
   b. transmitting the mixed modes after their emergence from the fluidic channel to detector;
   c. detecting a beat frequency generated by the mixed beam;
   d. measuring a relative phase difference, comprising measuring a phase of the detected beat frequency relative to a phase of a beat frequency of a reference signal, the beat frequency of the reference signal comprising a difference in frequency between the two orthogonally polarized modes of laser light; and
   e. detecting a DNA strand by correlating the relative phase difference with a change in effective refractive index of the host reagent caused by fractional change in the composition of host reagent because of inclusion of the selected gene/allele in the host reagent.

\* \* \* \* \*